US009295822B2

(12) United States Patent
Aggerholm

(10) Patent No.: US 9,295,822 B2
(45) Date of Patent: Mar. 29, 2016

(54) BALLOON CATHETER INCLUDING INNER AND OUTER BALLOONS

(75) Inventor: Steen Aggerholm, St. Heddinge (DK)

(73) Assignee: Cook Medical Technologies LLC, Bloomington, IN (US)

(*) Notice: Subject to any disclaimer, the term of this patent is extended or adjusted under 35 U.S.C. 154(b) by 549 days.

(21) Appl. No.: 12/956,521

(22) Filed: Nov. 30, 2010

(65) Prior Publication Data

US 2011/0130719 A1 Jun. 2, 2011

(30) Foreign Application Priority Data

Nov. 30, 2009 (GB) .................................. 0920997.4

(51) Int. Cl.
A61M 29/00 (2006.01)
A61M 29/02 (2006.01)
A61F 2/958 (2013.01)
A61M 25/10 (2013.01)

(52) U.S. Cl.
CPC .............. *A61M 29/02* (2013.01); *A61F 2/958* (2013.01); *A61M 25/1011* (2013.01); *A61M 2025/1013* (2013.01); *A61M 2025/1081* (2013.01); *A61M 2025/1086* (2013.01)

(58) Field of Classification Search
CPC .............. A61M 25/1011; A61M 2025/1013; A61M 2025/1059; A61M 2025/1075; A61M 2025/1084
USPC ............. 604/101.02, 103.08, 103.11, 103.12; 623/1.11, 1.12; 606/190–192, 194
See application file for complete search history.

(56) References Cited

U.S. PATENT DOCUMENTS

| | | | |
|---|---|---|---|
| 5,447,497 A | 9/1995 | Sogard et al. | |
| 5,868,776 A | 2/1999 | Wright | |
| 6,187,014 B1 | 2/2001 | Goodin et al. | |
| 2002/0042593 A1* | 4/2002 | Mickley et al. | 604/102.01 |
| 2006/0271093 A1* | 11/2006 | Holman | A61M 25/10 606/194 |

(Continued)

FOREIGN PATENT DOCUMENTS

| | | |
|---|---|---|
| EP | 1729684 B1 | 12/2010 |
| WO | 96/38109 | 12/1996 |

(Continued)

OTHER PUBLICATIONS

Combined Search and Examination Report under Sections 17 & 18(3), dated Mar. 29, 2010, pp. 1-3, issued in Great Britain Patent Application No. GB0920997.4, United Kingdom Patent Office, Newport, South Wales.

(Continued)

*Primary Examiner* — Katherine Rodjom
(74) *Attorney, Agent, or Firm* — Brinks Gilson & Lione

(57) ABSTRACT

An introducer assembly (10) includes a balloon catheter (12) for deploying a medical device (19) in a body lumen or for dilating a body lumen at a range of diameters from a minimum deployment diameter to a maximum deployment diameter. The balloon catheter includes an outer balloon (42) and an inner balloon (40) located within the outer balloon (42). The outer balloon (42) has an unstretched diameter equivalent to the minimum deployment diameter and the inner balloon (40) has an unstretched diameter equivalent to the maximum deployment diameter. The outer balloon (42) is made of an elastic material able to stretch from the minimum deployment diameter to the maximum deployment diameter, while the inner balloon (40) is preferably of an non-compliant material.

20 Claims, 3 Drawing Sheets

(56) References Cited

U.S. PATENT DOCUMENTS

2007/0299497 A1* 12/2007 Shaolian et al. ............. 623/1.11
2008/0255511 A1* 10/2008 Krivoruchko ............ 604/103.08

FOREIGN PATENT DOCUMENTS

WO 2009/036118 * 3/2009
WO 2009/036118 A1 3/2009

OTHER PUBLICATIONS

Combined Search and Examination Report under Section 18(3), dated Jul. 12, 2010, pp. 1-2, issued in Great Britain Patent Application No. GB0920997.4, United Kingdom Patent Office, Newport, South Wales.

* cited by examiner

BALLOON CATHETER INCLUDING INNER AND OUTER BALLOONS

TECHNICAL FIELD

The present invention relates to an introducer, hereinafter called a balloon catheter, for the deployment of implantable medical devices such as stents and stent grafts or for dilatation of a body lumen.

BACKGROUND ART

There is a variety of devices and mechanisms for deploying implantable medical devices in a lumen or other organ of a patient. For instance, in the case of stents and stent grafts, the device may be of a self-expandable type, in which case the device will expand by its own expansion force from a compressed delivery configuration to its expanded deployed condition. In order to ensure satisfactory anchoring to the lumen wall, the device typically has an expanded diameter which is larger than the diameter of the lumen. Thus, the device will maintain a constant expansion force against the lumen. This is not always considered advantageous.

Another arrangement provides a device which does no exhibit its own expansion force but is expanded by a separate mechanism, which is typically part of the introducer assembly. Such devices, for instance stents or stent grafts intended to be deployed in the aorta, can thus be expanded to a chosen diameter, typically the normal diameter of the aorta, and retain that diameter without imparting on the walls of the lumen any further expansion force which can be detrimental to the integrity of the lumen. A common mechanism to expand such devices is by means of a balloon catheter. Such a device provides a balloon at the end of the catheter, over which the radially compressed medical device is located. Inflation of the balloon expands the device to its deployed configuration.

There have been various disclosures of balloon catheters in the prior art. For instance, U.S. Pat. No. 5,868,776 discloses a balloon catheter having a double balloon structure provided with an inner balloon and an outer balloon. The inner balloon is made of a non-compliant material while the outer balloon is made of a stretchable material which is intended to provide a superior restoring force to aid in the deflation of the inner balloon, by providing a compressing force on the inner balloon, and it is explained that the outer balloon may always be taut.

U.S. Pat. No. 6,187,014 discloses a stent deployment device using a catheter with a double-layered balloon. The outer balloon is made of a compliant material whereas the inner balloon is made of a substantially non-compliant material. The structure provides for the outer, softer, balloon to be inflated first so as to deploy a stent. The outer balloon is then deflated, before the inner balloon is inflated. The inner balloon, which is stronger, is intended to set or fix the stent.

An advantage of balloon expandable medical devices, more particularly medical devices which are expanded by a separate expansion mechanism, is that they can provide a reliable and effective prosthesis which does not impart of the human body artificial stresses.

It is important with balloon expandable medical devices to be able to expand these to a predetermined diameter and it is equally important to be able to expand these in a manner such that they attain a properly rounded shape. In order to achieve this, the primary inflation balloon is typically made of a substantially non-compliant material. Such a material can provide the strong expansion force necessary to expand the medical device and also provides a reliable and predictable expanded shape, necessary to ensure proper deployment of the medical device.

This optimal characteristic of expansion balloons, however, involves a compromise in that the lumens of different patients vary in diameter. For instance, the aorta of an adult typically varies from around 22 mm in diameter to around 38 or 40 mm. This causes difficulties in the selection and provision of a suitable balloon. For instance, if a balloon is chosen which is larger than the diameter of the lumen, the balloon will not be fully expanded by the time the medical device has been expanded to the walls of the lumen and thus the balloon will not have attained its fully expanded state. Given the non-compliant nature of the balloon and the fact that it is typically wrapped onto the introducer for deployment, it is not possible to assure that the balloon has acquired its rounded configuration and that it will thus impart a full and complete rounded expansion force to the medical device. In such an event, it cannot be assured that the medical device will be properly deployed, that is pressed against the lumen wall across the entirety of its circumferential extent. This can therefore lead to less than optimum anchoring of the medical device to the lumen wall, with possible risks of migration, and can fail to provide patency of the device to the lumen wall, that is a proper seal of the device to the lumen wall, important for instance in the case of stent grafts.

On the other hand use of a balloon which has a diameter which is smaller than the lumen wall can lead to insufficient expansion of the medical device, inadequate anchoring and also inadequate sealing of the device to the lumen wall.

One method which can be used to seek to avoid these problems is to expand the medical device in stages, that is to start with a smaller diameter balloon, then to introduce a larger balloon into the lumen to expand the device further, continuing until the right sized balloon finally expands the device to the required diameter. It will be appreciated that this entails a multi-step expansion stage and thus a more elaborate deployment operation compared to a single stage operation.

Whilst in theory it might be possible to try to preselect a balloon of the correct diameter, in practice this is not always possible in light of the difficulties of being able to obtain an accurate measure of the internal diameter of a patient's lumen.

There is currently no structure which can resolve these issues.

SUMMARY OF THE PRESENT INVENTION

The present invention seeks to provide an improved introducer, in particular a balloon catheter, for the deployment of implantable medical devices such as stents and stent grafts in a body lumen or for dilating a body lumen.

According to an aspect of the present invention, there is provided a balloon catheter for deploying a medical device in a body lumen or for dilating a body lumen at a range of diameters from a minimum deployment or dilatation diameter to a maximum deployment or dilatation diameter, the balloon catheter including an outer balloon and an inner balloon located within the outer balloon; the outer balloon having an unstretched diameter equivalent to the minimum deployment or dilatation diameter and the inner balloon having an unstretched diameter equivalent to the maximum deployment or dilatation diameter; wherein the outer balloon is made of an elastic material able to stretch from the minimum to the maximum deployment or dilatation diameters.

Hereinafter the term deployment diameter is used to refer to a deployment or dilatation diameter.

The balloon catheter provides a double balloon structure in which the outer balloon becomes fully deployed at the minimum deployment diameter, for instance 22 mm in the case of an adult aortic medical device, that is fully unwrapped but not in a stretched condition. The inner balloon, on the other hand, is fully deployed at the maximum deployment diameter, in this example at, for instance, 26 mm. Thus, the outer balloon is able to effect deployment of a medical device in a "smaller" aortic lumen, in this example, while the inner balloon is able to deploy a medical device in an aortic lumen of greater diameter. The outer balloon is able to stretch from the minimum to the maximum deployment diameters and thus to provide a properly rounded support and deployment element between the inner and outer deployment diameters. The fact that the outer balloon has a diameter which is equivalent to the minimum deployment diameter has a number of advantages. First, the outer balloon does not need to stretch at all until the minimum diameter, thus contributing no effective restraining force on the balloon catheter. Secondly, it only needs to stretch by a relatively small amount from the minimum to the maximum deployment diameters, thus allowing the use of more robust outer balloon materials which are in themselves able to deploy a medical device, that is without the need for a stronger balloon element to complete the fixing of the medical device to the lumen. A more robust material may be a thicker material or a material which is less compliant, stretchable, than prior art balloon structures and thus one which is able to impart a sufficient deployment force on the medical device, for instance to ensure that this anchors properly to the lumen walls.

In practice, as explained above, the aorta of an adult can vary from around 22 mm in diameter to around 38 or 40 mm. It is envisaged that the teachings herein could provide a balloon catheter with a minimum deployment diameter of around 22 mm and a maximum deployment diameter of 38 or 40 mm, thus able to deploy a medical device in all expected sizes of adult aorta. In this instance, the balloon catheter will of course still provide the benefits taught herein and in which the outer balloon does not stretch until inflated beyond the minimum deployment diameter. In practice, however, it is envisaged that there would be provided a series of balloon catheters for different ranges of aorta sizes, particularly since there are typically provided different size stents, stent grafts or other medical devices, for the same reasons. Thus, in one embodiment, one balloon catheter is designed to have a minimum deployment diameter of around 22 mm and a maximum deployment diameter of 26 mm, there being provided one or more other balloon catheters with different ranges of deployment diameters, as an example only from 26 mm to 32 mm and from 32 mm to 38 or 40 mm.

An outer balloon which must stretch by a significant amount (for instance a plurality of times its non-stretched diameter) will necessarily have to be weaker and will generally be unable to effect proper and reliable deployment of a medical device without the assistance of a stronger, for instance non-compliant, balloon. It will also be appreciated that a structure which uses an outer balloon which stretches for most of the range of expansion of the inner balloon, for instance to assist in the deflation and rewrapping of the inner balloon, will always impart a restraining force, or deflationary pressure, on the balloon structure and thus impart resistance to the deployment operation necessitating a greater deployment force. Moreover, an outer balloon which has to stretch significantly will not generally provide a support structure which is solid enough itself to effect reliable deployment of the medical device.

In the case of a catheter assembly which provides a "reduced" range of operative diameters, that is for only a part of the entire expected range of aorta diameters, it will be appreciated that the outer balloon will only need to stretch by a relatively small amount and can thus be made of a thicker and stronger material.

Advantageously, the inner balloon is made of a substantially non-compliant material. The advantage of this structure is that it has in practice a maximum deployment diameter, for instance of 38 or 40 mm in the case of an aortic application, thus providing a reliable limit to the deployment size of the apparatus and thus prevent inadvertent over-expansion of the medical device.

It will be appreciated that the term non-compliant is intended to encompass both materials which exhibit virtually no compliancy in the range of inflation pressures to which such devices are subjected but also materials which show some compliancy but to a degree substantially less than the compliant (outer) balloon to behave in a substantially non-compliant manner. It is envisaged that in some embodiments the inner balloon could be made from a material expected to stretch by a certain amount during deployment. For instance, the outer balloon could have a minimum deployment diameter of 22 mm and the inner balloon an unstretched inflated diameter of 24 mm and stretchable to a maximum deployment diameter of 26 mm. Thus, the outer balloon will stretch by around 4 mm and the inner balloon by 2 mm.

Preferably, the catheter includes an inflation lumen arranged to inflate only the inner balloon. With this structure it is not necessary to inflate the outer balloon separately. In fact, it is preferred to rely upon inflation of the relatively non-compliant inner balloon to effect the expansion of the outer balloon and of the implantable medical device, thus to provide a reliable inflation arrangement.

The outer balloon may be vented or porous. This has the advantage that the diameter to which the outer balloon is deployed, whether unstretched or stretched, is virtually the same as the diameter of the inner balloon element. Moreover, the double balloon structure can be tightly wrapped as well as rewrapped after deployment of the medical device.

In an embodiment, the catheter is an aortic deployment catheter and the minimum and maximum deployment diameters are around 24 mm and around 26 mm respectively. It will be appreciated that these diameters will be dependent upon the lumen and the variation in dimensions of such a lumen from one person to another.

Advantageously, the outer balloon stretches between the minimum and maximum deployment diameters by no more than around 25% of its unstretched dimension. Preferably the outer balloon stretches by no more than around 10%.

In the preferred embodiment, the inner and outer balloons have a non-deployed configuration in which they are both in a wrapped condition.

According to another aspect of the present invention, there is provided an introducer assembly including a balloon catheter for deploying a medical device in a body lumen at a range of diameters from a minimum deployment diameter to a maximum deployment diameter, the balloon catheter including an outer balloon and an inner balloon located within the outer balloon; the outer balloon having an unstretched diameter equivalent to the minimum deployment diameter and the inner balloon having an unstretched diameter equivalent to the maximum deployment diameter; wherein the outer balloon is made of an elastic material able to stretch from the minimum deployment diameter to the maximum deployment diameter.

Advantageously, the inner and outer balloons have a non-deployed configuration in which they are both in a wrapped condition.

Preferably, the catheter or assembly includes a medical device fitted over the balloon structure with the inner and outer balloons in a wrapped condition.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Figure 1:
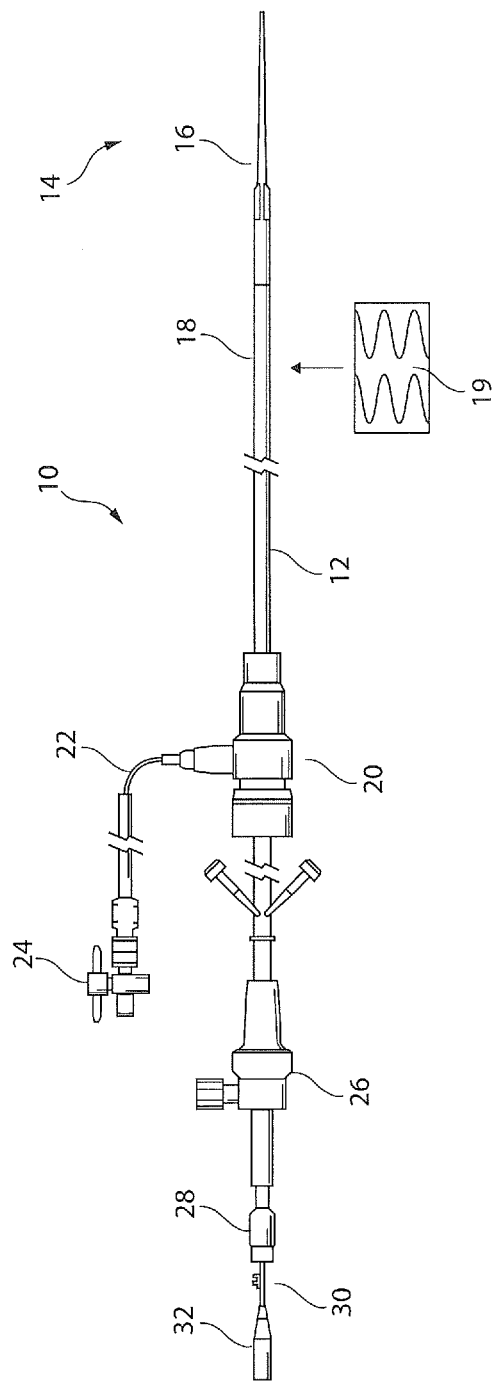
FIG. 1 shows a schematic view of an example of balloon catheter introducer assembly.

Referring to FIG. 1, there is shown an embodiment of introducer apparatus including a balloon catheter. The apparatus 10 includes a catheter 12 having a distal end 14 provided with a dilator tip 16 of conventional type and a balloon structure 18 at the distal tip, described in further detail below. The balloon 18 is shown in a wrapped configuration at the distal end of the catheter and lying underneath a medical device 19, in this example a stent graft.

At a proximal end of the catheter 12, typically an external manipulation end, there is provided apparatus of conventional form, including a haemostatic valve assembly 20 with a fluid feed tube 22 provided with a stop lock 24. The assembly also includes a trigger wire release mechanism 26, a pin vise 28 for fixing an inner cannula 30 at the proximal end of which there is provided a hub 32 for a guide wire. The components of the distal end of the introducer assembly, being of conventional form, are not described in further detail herein.

Figure 2:
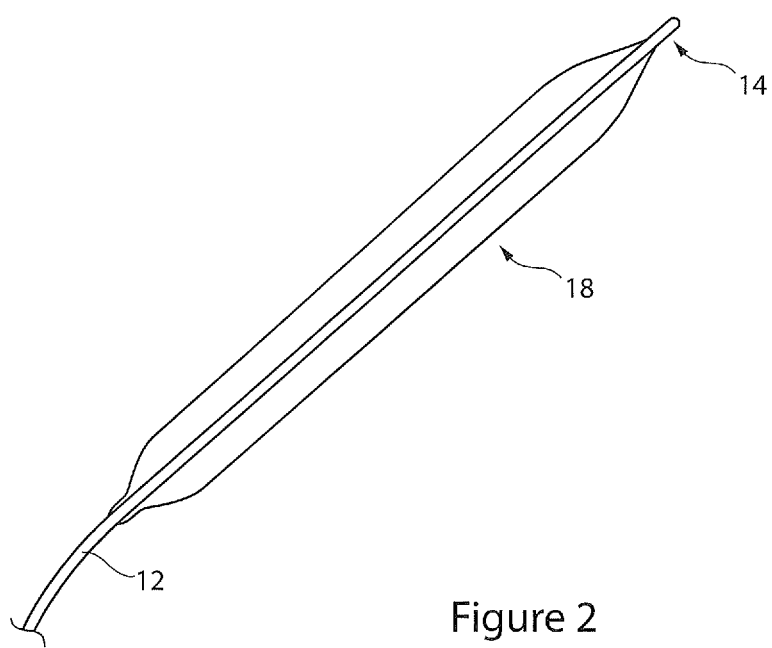
FIG. 2 is an enlarged view of an example of balloon catheter tip.

FIG. 2 shows an enlarged view of an example of balloon structure 18 at the distal end 14 of the catheter 12. As can be seen, it is typical for the balloon structure 18 to have a substantially circular cylindrical form and which is secured at its ends to the catheter 12. The balloon 18 is typically made of a substantially non-compliant material so that its expanded diameter is of a known size, thereby providing a reliable and repeatable expansion diameter for the medical device expanded thereby. In practice, the medical device is fitted over the balloon structure 18 when the latter is in a deflated and wrapped configuration on the balloon catheter 12, again in known manner.

Figure 3:
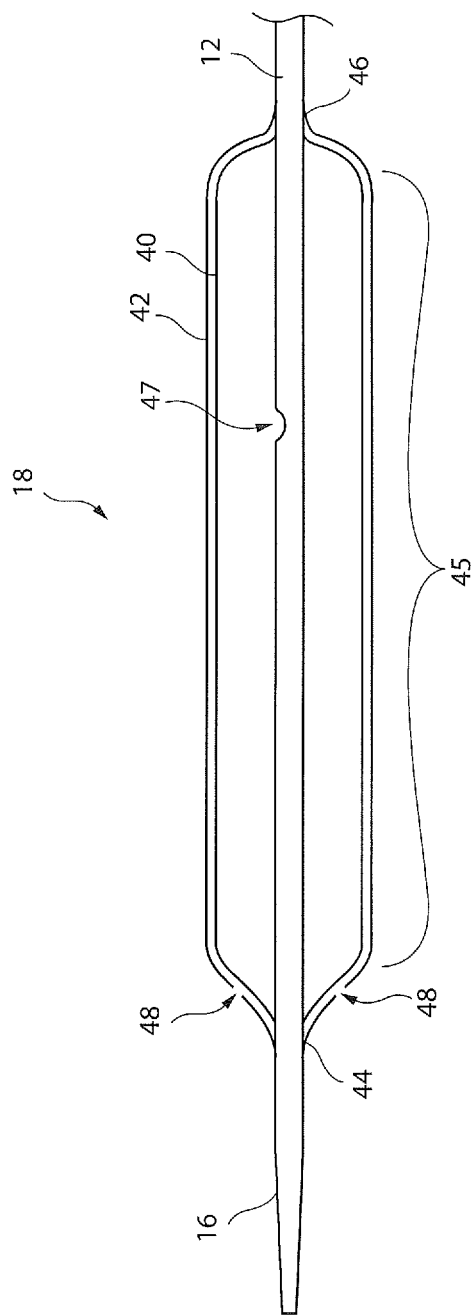
FIG. 3 is a schematic view of a preferred embodiment of balloon catheter.

Referring now to FIG. 3, there is shown a preferred embodiment of balloon structure 18, which is formed of inner and outer balloons 40 and 42 respectively. In FIG. 3 the balloons 40, 42 are shown being spaced from one another, for the purposes of ease of explanation only. In practice, the balloons 40, 42 will touch one another, typically in all configurations but at the least from when the outer balloon 42 is in its expanded condition.

The inner balloon 40 fits completely within the space of the outer balloon 42 and may share the same fixing points 44, 46 at the two ends of the balloon structure 18.

The outer balloon 42 has an expanded diameter, hereinafter referred to as the first or minimum deployment diameter, which is selected to correspond substantially with a minimum expected diameter of the lumen type into which the medical device 19 is to be fitted. In the case of an aortic device for an adult, this diameter will typically be in the region of 24 millimeters. It will be appreciated that the minimum deployment diameter may be a little greater than the minimum expected diameter of the lumen in order to ensure good fitting and anchoring of the medical device to the lumen walls.

The inner balloon 40 has an expanded diameter, hereinafter referred to as the second or maximum deployment diameter, which is selected to correspond substantially with a maximum expected diameter of the lumen type into which the medical device 19 is to be fitted. In the case of an aortic device for an adult, this diameter will typically be in the region of 26 millimeters. It will again be appreciated that the maximum deployment diameter may be a little greater than the maximum expected diameter of the lumen in order to ensure good fitting and anchoring of the medical device to the lumen wall.

The balloon structure 18 preferably has a length at least as long as the length of the medical device 19 to be carried thereon and expanded thereby. Typically, the balloon structure 18 will be longer than the medical device 19, such as to ensure that the medical device is supported and expanded by the cylindrical part 45 of the balloon structure 18.

The outer balloon 42 is made from a compliant material thus able to stretch when pressure or force is applied thereto. This balloon may typically be made of polyurethane, Pebax, soft Nylon, latex or silicone, although any suitable compliant material could be used.

The inner balloon 40, on the other hand, is preferably made from a substantially non-compliant material, for instance polyurethane Nylon, Pebax or polyurethane, and is of a type, material or structure which provides relative non-compliancy compared to the outer balloon 42. It will be appreciated that any other suitable non-compliant material may be used. It is to be understood that the inner balloon may be formed from a material which does exhibit some compliancy. The term non-compliant as used herein is intended to encompass materials and structures which will exhibit, at the pressures to which the balloon 40 is inflated, virtually no noticeable expansion on inflation compared to the expansion of the outer balloon 42.

In some embodiments, the inner and/or outer balloons 40, 42 may be multi-layered structures.

The catheter 12 includes a lumen therein (not shown but of conventional form) which includes a port 47 which couples to the interior of the inner balloon 40. There is, in the preferred embodiment, no port or lumen feeding into the outer balloon 42, that is to the location between the inner and outer balloons 40, 42.

The lumen and port 47 provide an inflation fluid into the inner balloon 40 and, in some embodiments, also a deflation vacuum. It will be appreciated that in the preferred embodiment there is no separate inflation of the outer balloon 42 and thus that only the inner balloon 40 is inflated.

The outer balloon 42 may include one or more apertures or ports 48 in the balloon wall and/or may be made of a porous material. Thus, the outer balloon 42 cannot be inflated and will trap no fluid between it and the inner balloon 40.

The balloon structure 18, that is the inner and outer balloons 40, 42 are typically wrapped in a manner analogous to conventionally wrapped balloons. In the preferred embodiment, the inner and outer balloons 40, 42 are wrapped together such as to have interleaved folds.

When it is desired to deploy a medical device 19 in a lumen, once the distal end of the catheter 12 has been located at the treatment site in the patient, the medical device is released from locking engagement with the introducer, in this example by release of one or more trigger wires. Inflation pressure is then applied into the inner balloon 40 through the port 46, typically by pumping saline solution or contrast media (either 100% or typically up to around 50% with saline solution) into the inner balloon 40. Thus, the inner balloon 40 will begin to expand and in so doing will expand the outer balloon 42 as well as the medical device 19 carried thereon. The inner balloon 40 will continue to expand through a condition in which the outer balloon 42 becomes fully expanded, that it to the minimum deployment diameter. Up to this point, the outer balloon is not stretched and thus will not impart on the inner balloon 40 or the inflation device any deflationary or constricting pressure. The outer balloon 42 will simply unwrap and will eventually attain a circular cylindrical form, suitable for deploying the medical device 19 carried thereon. The inner balloon 40 applies on the outer balloon 42 an expansion force sufficient for the latter's expansion as well as to ensure proper deployment and anchoring of the medical device 19 to the lumen walls. It is to be appreciated that this can be achieved with no other fixation mechanism being necessary or used.

Fixation of a stent-graft can be achieved sufficiently reliably and accurately that it is not necessary to have any bare stent on the device, as is necessary in some prior art devices.

Should the patient's lumen have a diameter no greater than the minimum deployment diameter, the inflation stage can end at this point and the inner balloon then deflated to remove the introducer assembly 10 from within the patient. Depending upon the device 19 tying arrangement provided, it may be necessary beforehand to complete the release of the device 19 from the introducer 10, for instance by release of one or more trigger wires. Methods of fixing a device 19 to a balloon catheter are well known in the art.

Should the patient's lumen be greater than the minimum deployment diameter, the inner balloon 40 is inflated beyond this diameter towards the maximum deployment diameter. Inflation beyond the minimum inflation diameter involves the stretching of the outer balloon 42. The inner balloon 40, by virtue of its greater expanded diameter, will continue to unwrap from the minimum to the maximum deployment diameters, that is while the outer balloon 42 stretches. During this phase, therefore, the balloon structure 18 will retain a smooth circular cylindrical outer surface by virtue of the complete expansion, and stretching, of the outer balloon 42 and thus provide an even and reliable expansion surface for expanding the medical device 19 in a round cylindrical form.

The apertures or pores of the outer balloon 42 ensure that this expands under the control of the inner balloon 40 and therefore with a diameter which is consistent with that of the inner balloon 40. It is not necessary to vent the zone between the inner and outer balloons 40, 42 by any separate mechanism as this will occur naturally.

The outer balloon 42 will provide some deflation pressure on the inner balloon 40 after it has been stretched beyond the minimum deployment diameter, thereby assisting in the deflation of the balloon structure. It is also envisaged that the inner and outer balloons 40, 42 may be coupled to one another along their lengths, for instance by spot bonding or some other mechanism, such that the outer balloon 42 will be pulled to a rewrapped configuration on deflation of the inner balloon 40. The balloons 40, 42 may alternatively or additionally be formed with an unexpanded elongate ribbed form to assist in rewrapping, that is a form in which the walls of the balloons 40, 42 have longitudinally extending ribs or corrugations providing partial folds in the absence of inflation pressure.

It will be appreciated that the outer balloon 42 does not need to stretch by a significant amount in this structure, typically by no more than 25% and in some cases by no more than around 10%. It is therefore not necessary to form the outer balloon 42 of a highly compliant material or with walls so thin that they can stretch by a significant extent. Therefore, the outer balloon 42 can have a wall strength which will provide a firm and reliable expansion support for deploying a medical device 19 properly into a lumen and ensure proper anchoring of the device, without having to use or rely upon fixing by means of a non-compliant balloon as is the case with some prior art devices. Therefore, the device 10 can provide reliable deployment of a medical device 19 at any deployment diameter from the minimum to the maximum deployment diameters and thus deployment in a variety of lumen sizes, typically any size for that type of lumen. This can be achieved in a single deployment stage.

Although the preferred embodiments have been shown in connection with a balloon structure 18 of generally cylindrical form it will be appreciated that they are not limited to this and could be applied to balloons having non-cylindrical shapes, for instance tapering or of otherwise varying outer diameter.

Although the embodiments above relate to a balloon catheter and introducer for the implantation of a medical device into a lumen of a patient, the balloon catheter need not be for implantation purposes. For instance, the balloon catheter could be used for dilation procedures such as angioplasty procedures, post dilatation procedures, oesophagus treatment. It can also be used for AAA products and embolisation treatments.

What is claimed is:

1. A balloon catheter for deploying a medical device in or for dilating a body lumen at a range of diameters from a minimum deployment or dilatation diameter to a maximum deployment or dilatation diameter, wherein the minimum deployment or dilatation diameter is selected to correspond substantially with a minimum expected diameter of a lumen type into which the medical device is to be fitted and the maximum deployment or dilatation diameter is selected to correspond substantially with a maximum expected diameter of the lumen type into which the medical device is to be fitted; the balloon catheter including a catheter body, an outer balloon having a proximal end and a distal end which are fixed to the catheter body and an inner balloon fixed to the catheter body located within the outer balloon; the outer balloon having an unstretched inflated diameter equivalent to the minimum deployment or dilatation diameter and the inner balloon having an unstretched inflated diameter equivalent to the maximum deployment or dilatation diameter; wherein the outer balloon is made of an elastic material able to stretch from the minimum to the maximum deployment or dilatation diameters; and wherein the elastic material of the outer balloon is uninflatable and is one of: vented and porous, and the inner balloon is made of an inflatable material that is not vented or porous;

wherein a minimum inflation applied to the inner balloon expands the inner and outer balloons to the minimum deployment or dilatation diameter at which the outer balloon is unstretched and attains a smooth outer surface, inflation beyond the minimum inflation stretching the outer balloon as the inner balloon unwraps from the minimum deployment or dilatation diameter to the maximum deployment or dilatation diameter, the outer balloon retaining the smooth outer surface from the minimum deployment or dilatation diameter to the maximum deployment or dilatation diameter; and wherein there is no port or lumen in the catheter body to feed an interior location between the inner balloon and the outer balloon.

2. A balloon catheter according to claim 1, wherein the inner balloon is made of a substantially non-compliant material.

3. A balloon catheter according to claim 1, including an inflation lumen arranged to inflate only the inner balloon.

4. A balloon catheter according to claim 1, wherein the catheter is an aortic deployment catheter.

5. A balloon catheter according to claim 4, wherein the minimum and maximum deployment or dilation diameters are around 22 mm and around 26 mm respectively.

6. A balloon catheter according to claim 1, wherein the minimum and maximum deployment or dilatation diameters are around 22 mm and around 38 or 40 mm respectively.

7. A balloon catheter according to claim 1, wherein the outer balloon stretches between the minimum and maximum deployment or dilatation diameters by no more than around 25% of its unstretched dimension.

8. A balloon catheter according to claim 1, wherein the outer balloon stretches between the minimum and maximum deployment or dilatation diameters by no more than around 10% of its unstretched dimension.

9. A balloon catheter according to claim 1, wherein the inner and outer balloons have a non-deployed configuration in which they are both in a wrapped condition.

10. A balloon catheter according to claim 9, including a medical device fitted over the balloon structure with the inner and outer balloons in a wrapped condition.

11. A balloon catheter according to claim 1, wherein the outer balloon and the inner balloon are fixed to a common point on the body of the catheter.

12. The balloon catheter of claim 1, wherein the outer balloon has a wall thickness which is greater than a wall thickness of the inner balloon.

13. The balloon catheter of claim 1, wherein when the outer balloon is unstretched, the smooth outer surface comprises a cylindrical portion which is not vented or porous.

14. A balloon catheter for deploying a medical device in or for dilating a body lumen at a range of diameters from a minimum deployment or dilatation diameter to a maximum deployment or dilatation diameter, wherein the minimum deployment or dilatation diameter is selected to correspond substantially with a minimum expected diameter of a lumen type into which the medical device is to be fitted and the maximum deployment or dilatation diameter is selected to correspond substantially with a maximum expected diameter of the lumen type into which the medical device is to be fitted; the balloon catheter including a catheter body, an outer balloon and an inner balloon located within the outer balloon; the outer balloon having an unstretched inflated diameter equivalent to the minimum deployment or dilatation diameter and the inner balloon having an unstretched inflated diameter equivalent to the maximum deployment or dilatation diameter; wherein the outer balloon is made of an elastic material able to stretch from the minimum to the maximum deployment or dilatation diameters; and wherein the elastic material of the outer balloon is uninflatable, and the inner balloon is made of an inflatable material, wherein there is no port or lumen in the catheter body to feed an interior location between the inner balloon and the outer balloon;

wherein a minimum inflation applied to the inner balloon expands the inner and outer balloons to the minimum deployment or dilatation diameter at which the outer balloon is unstretched and comprises an outer surface comprising a smooth cylindrical portion, a proximal portion, and a distal portion, wherein inflation beyond the minimum inflation stretching the outer balloon as the inner balloon unwraps from the minimum deployment or dilatation diameter to the maximum deployment or dilatation diameter, the outer balloon retaining the smooth outer surface from the minimum deployment or dilatation diameter to the maximum deployment or dilatation diameter; and wherein the outer surface of the outer balloon comprises a port located only on the proximal portion and distal portion.

15. The balloon catheter of claim 14, wherein the proximal portion of the outer surface of the outer balloon is coupled to a body of the catheter.

16. The balloon catheter of claim 14, wherein the distal portion of the outer surface of the outer balloon is coupled to a body of the catheter.

17. The balloon catheter of claim 14, wherein the smooth cylindrical portion of the outer surface of the outer balloon is configured to engage an inner surface of a device.

18. The balloon catheter of claim 14, wherein the outer balloon has a wall thickness which is greater than a wall thickness of the inner balloon.

19. The balloon catheter of claim 14, wherein in an undeployed configuration, the inner balloon comprises a fold.

20. The balloon catheter of claim 19, wherein in the undeployed configuration, the inner balloon and the outer balloon are wrapped together such as to have interleaved folds.

* * * * *